(12) United States Patent
Gelfand et al.

(10) Patent No.: US 6,480,009 B1
(45) Date of Patent: Nov. 12, 2002

(54) SOLIDS MEASUREMENT SYSTEM

(75) Inventors: Mikhail Gelfand, Milford; Richard Opalanko, Trumbull; Kenneth Engquist, Hamden, all of CT (US); William F. Schwartz; Alexander Probst, both of Bailey, CO (US)

(73) Assignee: GL&V/ Dorr-Oliver Inc., Milford, CT (US)

( * ) Notice: Subject to any disclaimer, the term of this patent is extended or adjusted under 35 U.S.C. 154(b) by 3 days.

(21) Appl. No.: 09/711,428

(22) Filed: Nov. 13, 2000

Related U.S. Application Data

(60) Provisional application No. 60/164,711, filed on Nov. 11, 1999.

(51) Int. Cl.[7] .............................................. G01R 27/02
(52) U.S. Cl. ......................... 324/724; 324/445; 73/866
(58) Field of Search ................................ 324/437, 453, 324/445, 446, 724; 73/866

(56) References Cited

U.S. PATENT DOCUMENTS

| | | | |
|---|---|---|---|
| 3,685,654 A | * 8/1972 | MacLellan et al. | ......... 210/528 |
| 4,402,350 A | * 9/1983 | Ehret et al. | .................. 137/554 |
| 5,077,525 A | * 12/1991 | West et al. | .................. 324/204 |
| 5,325,709 A | * 7/1994 | Lynden | ...................... 422/68.1 |

* cited by examiner

Primary Examiner—N. Le
Assistant Examiner—Vincent Q. Nguyen
(74) Attorney, Agent, or Firm—McCormick, Paulding & Huber LLP

(57) ABSTRACT

In a solids profile measurement system for determining the quality of a solids bed formed from a liquid-solid slurry in a vessel, a sensor adapted to generate signals indicative of a profile as measured by progressively immersing the sensor deeper into the slurry is provided. An extension mechanism, at least a portion of which is coupled at one end to the sensor and at an opposite end to a piece of processing equipment, is provided to affect retrograde movement in a first direction to immerse the sensor in a slurry, and in a second direction opposite the first direction. A controller in communication with the extension mechanism is also provided and issues commands thereto and receives signals generated by the sensor.

21 Claims, 3 Drawing Sheets

SOLIDS MEASUREMENT SYSTEM

CROSS REFERENCE TO RELATED APPLICATION

This application claims priority under 35 U.S.C. §119(e) to U.S. Provisional Patent Application Serial No. 60/164,711, Filed Nov. 11, 1999 entitled SOLIDS PROFILE MEASUREMENT SYSTEM of Mikhail Gelfand et al.

BACKGROUND OF THE INVENTION

Different types of processing equipment, particularly those used in waste water treatment, involve settling tanks and the like wherein a slurry consisting of a carrier liquid and suspended solids is introduced into the piece of equipment. The suspended solids are allowed to settle to the bottom of the tank into which the slurry is introduced. The solids tend to settle along a gradient with the solids' concentration as well as composition changing as the bottom or floor of the tank is approached. Typically, the density of solids is highest at the bottom of the tank and then progressively falls towards the surface of the slurry. The quality and consistency of this solids layer and the manner in which the solids density progressively increases towards the bottom of the tank, has a bearing on how the solids layer will be subsequently processed.

For example, in large settling tanks that employ rake arms and pumping systems to draw off the solids layer, the denser the layer, the more power required by the pump and potentially the larger the pump needs to be. Accordingly, a reliable indication of the consistency and manner in which the solids have settled to the bottom of a given receptacle is required to not only size any down stream process equipment but also to appropriately operate any process equipment. For example, if the solids layer is removed too quickly, the clarified carrier liquid will also be drawn off, or if, on the other hand, the material is removed too slowly, then the density of the solids may become too great for the downstream equipment to handle.

Efforts to accurately measure the quality of the solids layer at the bottom of a container have proven difficult because placement of the measurement device, as well as the type of measurement device, have in general not been accurate enough. Based on the foregoing, it is the general object of the present invention to overcome the drawbacks and problems associated with known prior art solids profile measurement systems.

It is a more specific object of the present invention to employ an accurate sensing device in conjunction with a precise positioning mechanism in order to obtain consistent and reliable solids profile consistency data.

SUMMARY OF THE INVENTION

The present invention is directed to a solids profile measurement system for determining the quality of a solids bed formed from a liquid-solid slurry along a lower surface of a vessel containing the slurry. In general, the vessel will form part of a piece of processing equipment for handling the slurry, with said measurement system including a sensor adapted to generate signals indicative of a profile as measured by progressively immersing the sensor deeper into the slurry. The profile is formed by solids settling out of the slurry towards a bottom surface of the vessel. The solids establish a gradient between the bottom surface and the upper surface of the slurry. Extension means are provided wherein at least a portion of which is coupled at one end to the processing equipment and at an opposing end to the sensor. The extension means affect retrograde movement in a first direction, thereby immersing the sensor into the slurry. The extension means can also move the sensor in a second direction opposite to the first direction. A controller is in communication with the extension means and the sensor for issuing commands thereto and receiving signals generated by the sensor. In the preferred embodiment of the present invention, the extension means is also moveable back and forth across the vessel in response to commands issued from the controller in order to map the entire solids profile.

Preferably, the above-described extension means includes a pantograph mechanism having the sensor attached at one end thereto. Drive means, in communication with the pantograph mechanism, cause the mechanism to move the sensor in the first or second directions in response to commands issued from the controller. The drive means may include a cylinder having a rod slidably mounted therein and attached at an end thereof to the pantograph mechanism. The rod is moveable between an extended and retracted position, thereby causing the pantograph mechanism to move in the first and second directions. The cylinder can be either pneumatic or hydraulic; however, the present invention is not limited in this regard.

In an embodiment of the present invention, the extension means instead of the above-described pantograph mechanism includes a rod having the sensor coupled at one end thereto and an actuator coupled to a support that extends across the vessel. The rod and actuator communicate with one another such that the actuator moves the rod between a raised and lowered position in response to commands issued from the controller. It is preferable that the rod and actuator also be moveable back and forth along the support that spans the vessel, thereby allowing complete mapping of the solids profile. In addition, it is further preferable that the actuator be a stepper-type motor responsive to commands issued from the controller; however, the present invention is not limited in this regard.

In yet another embodiment, the extension means takes the form of a reel rotatably coupled to a mounting bracket that is in turn mounted to the particular piece of processing equipment that includes the vessel having the liquid-solid slurry contained therein. A length of flexible cable is wound about the reel and has the sensor coupled to an end thereof. An actuator is attached to the reel for rotating the wheel and causing the flexible cable, and thereby the sensor, to move in the first or second direction. The cable is positioned over a sheeve, also coupled for rotation to the mounting bracket and having an optical encoder in communication with the sheeve. During operation, the rotary encoder generates signals indicative of the number of rotations of the sheeve, said signals being receivable by the controller and thereby converted into a linear distance traveled by the sensor into or out of the slurry.

DETAILED DESCRIPTION OF THE PREFERRED EMBODIMENTS

Figure 1:
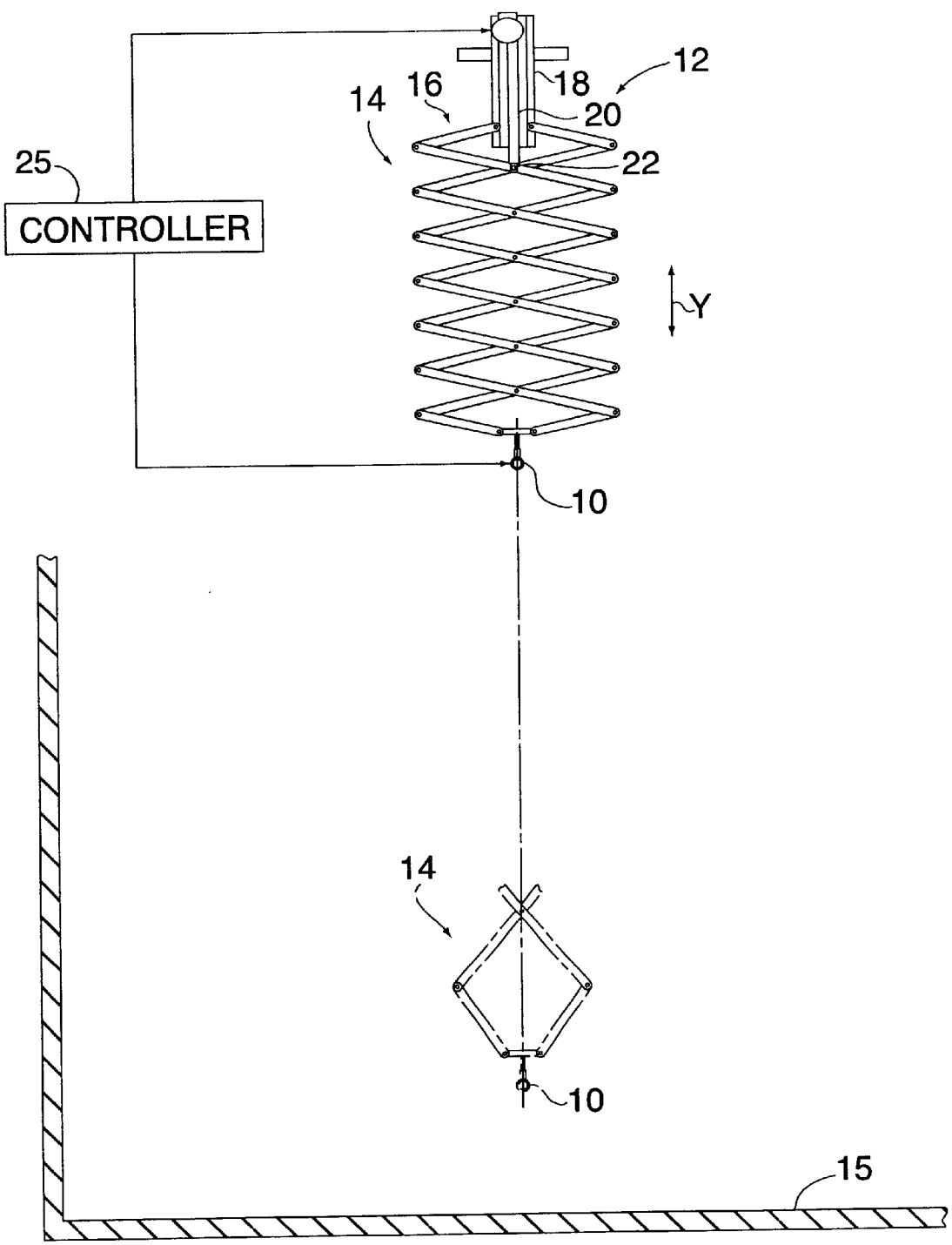
FIG. 1 schematically illustrates a solids profile measurement device in accordance with the present invention coupled to a positioning mechanism also in accordance with the present invention and movable between an extended and retracted position.

As shown in FIG. 1, the apparatus of the present invention employs an inductive conductivity sensor 10 to detect and determine the profile of the solids bed. Shown more clearly in FIG. 3 the inductive conductivity sensor 10 is known in the art and sometimes referred to as a toroidal conductivity sensor because of the shape of the coils used in the sensor. The profile of the solids is determined from the conductivity of the material using known methods. To accomplish this, the sensor is mounted to a bridge (not shown) of a thickener or clarifier for movement back and forth along the bridge in response to commands issued from a controller (not shown), as explained in detail hereinbelow. During operation, the inductive conductivity sensor 10 is also moved up and down, as indicated by the arrow labeled "Y", by an extension or movement system generally designated by the reference number 12.

In the preferred embodiment of the present invention, the movement system 12 includes a scissor-like or pantograph mechanism 14 attached at an upper end 16 to a cylinder 18. The cylinder 18 includes a rod 20 movable between an extended and retracted position. The rod 20 is coupled to the pantograph mechanism 14 at an end 22 such that movement of the rod causes a concomitant movement of the pantograph mechanism. Due to the scissor-like construction of the pantograph mechanism 14, retrograde movement of the rod 20 in the direction Y over a known first distance causes movement of the sensor 10 over a second distance. The cylinder can be either hydraulically or pneumatically actuated.

The second distance has a magnitude greater than the first distance and in the preferred embodiment of the present invention is approximately six (6) times greater than the magnitude of the first distance. However, the present invention is not limited in this regard as the ratio of sensor to rod movement can assume any practically attainable value without departing from the broader aspects of the present invention. Preferably, the movement system is mounted to a support or a bridge (not shown) that extends across the vessel 15 containing the slurry. The movement mechanism is moveable in response to commands issued from the controller 25 back and forth along the support such that the sensor can map the entire solids profile contained within the vessel 15. At certain predetermined locations, the sensor 10 is lowered via the pantograph mechanism to sense the profile of the settled solids in the processing equipment. Signals generated by the sensor 10 are received by the controller 25.

Preferably, the controller 25 of the present invention is a programmable logic controller or PLC. The PLC is programmed to optimize the motion of the sensor such that the sensor is in a fixed location for the minimum time necessary to obtain a precise signal. The PLC can determine several process parameters using known methods based upon the signals received from the sensor 10. Among these parameters are:

Solids Load
   A measure of the total solids content in the thickener;
Maximum Percent Solids
   The highest percent solids reading in the solids profile;
Compaction Level
   The demarcation point between the loose solids phase and the phase containing fully compacted solids;
Interface Clarity
   A measure of the quality of the interface level;
Compaction Level Clarity
   A measure of the quality of the compaction interface level;
Interfacial Zone Size
   A measure of the size of the region of loose solids;
Compaction Zone Size
   A measure of the size of the region of fully compacted solids;
   $_{13}$Interface—The rate of change of the interface;
   $_{13}$Load—The rate of change of the thickener load; However, the present invention is not limited in this regard as other parameters known to those skilled in the pertinent art to which the invention pertains can also be measured.

Figure 2:
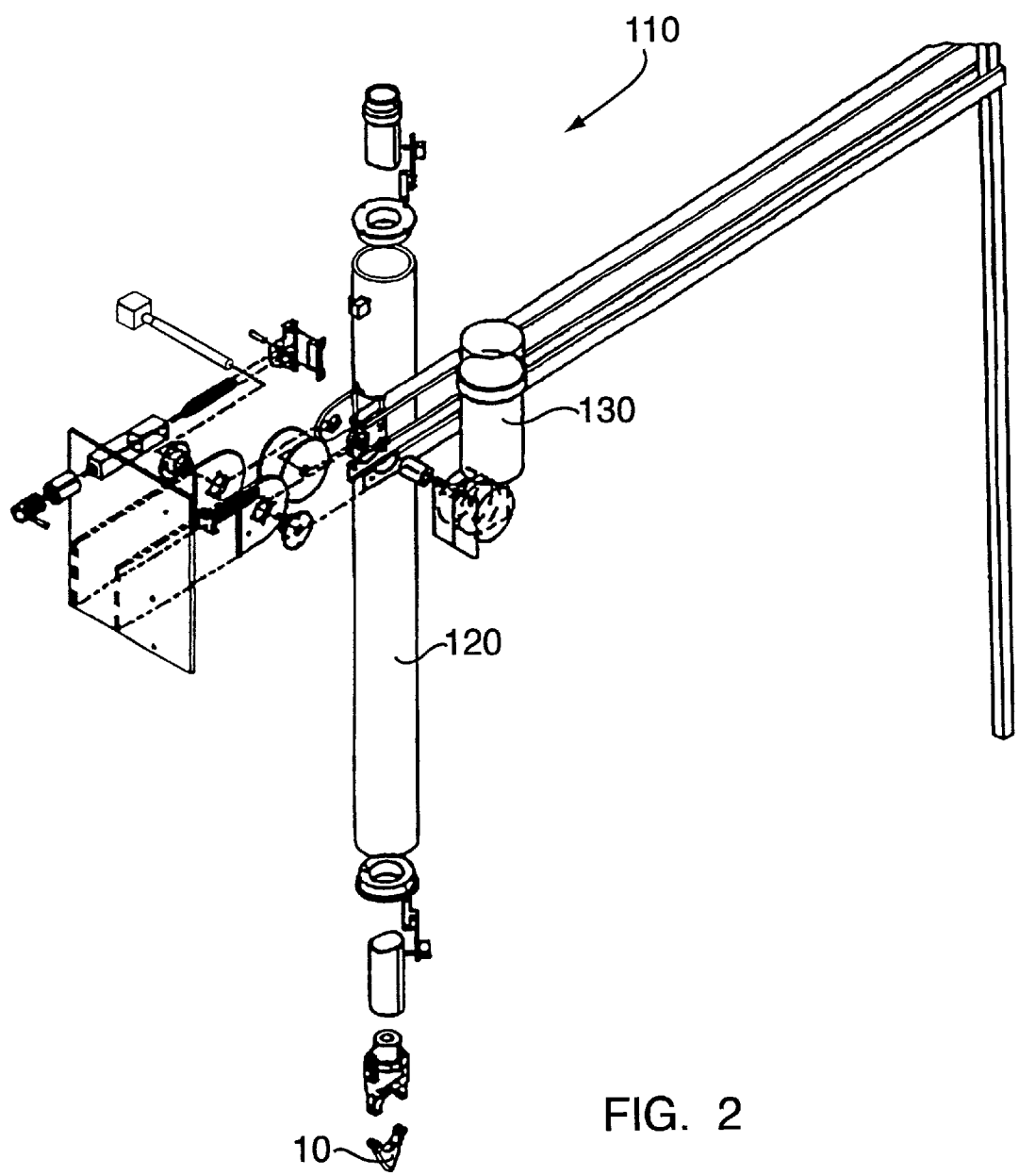
FIG. 2 is an exploded parts view illustrating an alternate embodiment of the solids profile measurement system of the present invention.

While a movement system 12 including a scissor-like or pantograph mechanism 14 has been shown and described, the present invention is not limited in this regard. As shown in FIG. 2, an alternate embodiment of the movement mechanism 110 includes a rod 120 movable via a suitable drive, such as, but not limited to a motor 130. An inductive conductivity sensor 10 is mounted to an end of the rod 120. During operation, the bar is lowered at predetermined points, into the process equipment so that readings can be taken by the sensor 10.

Figure 3:
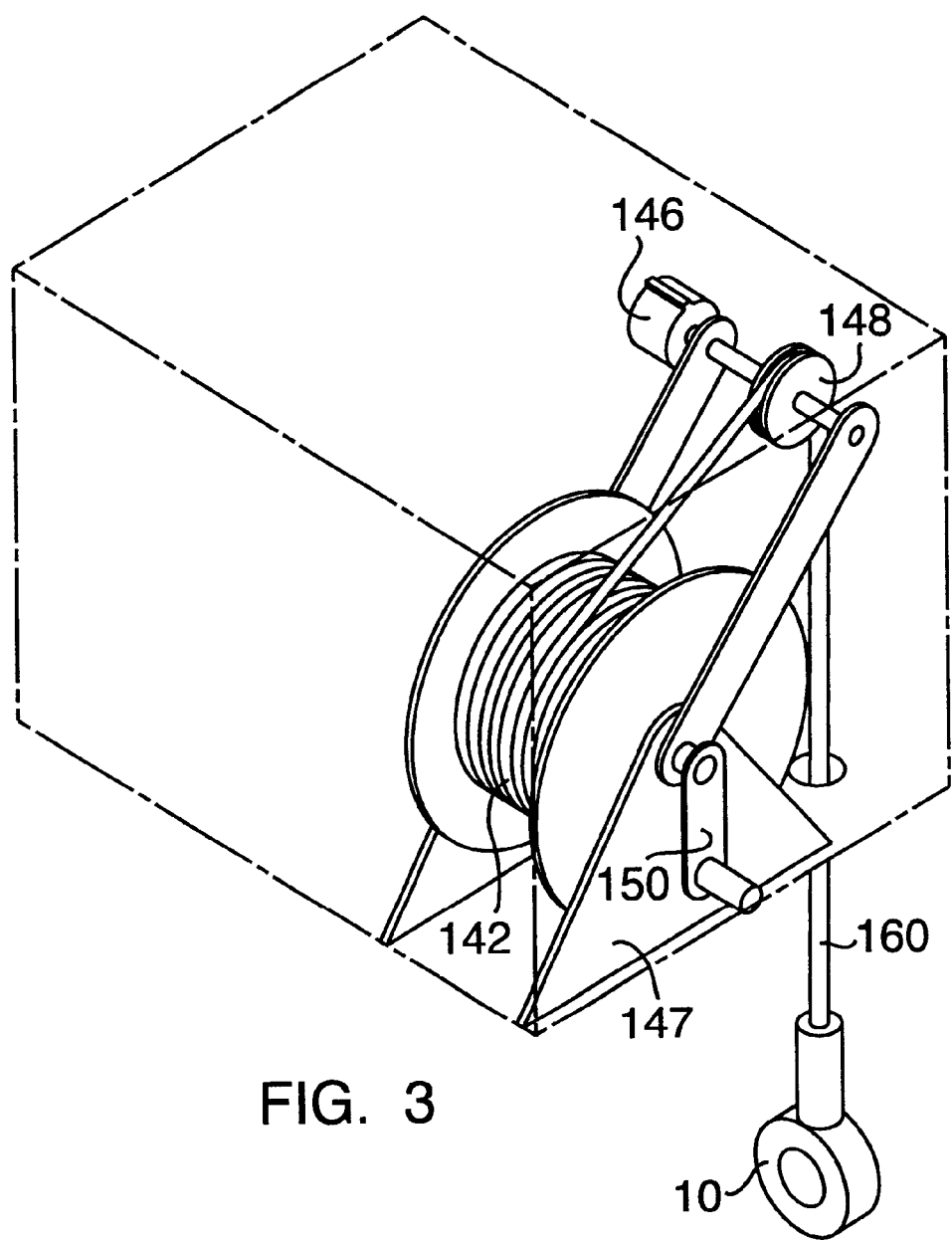
FIG. 3 is a perspective, partially schematic view of yet another embodiment of the solids profile measurement system of the present invention.

Another embodiment of the present invention is shown in FIG. 3, and employs a reel 142 and flexible cable 160 to lower the sensor 10 into the process equipment. The reel is rotatably mounted to a mounting bracket 147. A sheeve 148 is also rotatably mounted to the bracket and the cable 160 passes over the sheeve 148. The rotary encoder 146 communicates with the sheeve as well as the controller 25 so that rotary motion of the sheeve 148 can be converted into the linear distance at which the sensor 10 is raised or lowered into the slurry. An actuator 150, shown in the illustrated embodiment as a manually operated handle, is also provided to effect the upward or downward movement of the sensor. While a handle 150 has been illustrated, the present invention is not limited in this regard as other types of actuators, such as stepper motors, can be employed without departing from the broader aspects of the present invention.

While preferred embodiments have been shown and described, various modifications and substitutions may be made without departing from the spirit and scope of the invention. Accordingly, it is to be understood that the present invention has been described by way of example, and not by limitation.

What is claimed is:

1. A solids measurement system for selectively measuring the conductivity of a liquid-solid slurry throughout a vessel containing the slurry, the system comprising:

a vessel containing a liquid-solid slurry;

an inductive conductivity sensor adapted for generating signals indicative of the conductivity of the slurry;

extension means supporting said sensor for effecting retrograde movement in a first direction for progressively immersing said sensor in the slurry, and for affecting movement in a second direction opposite said first direction;

a controller in communication with said extension means and said sensor for controlling the motion of said extension means and for receiving said signals generated by said sensor;

said extension means movable back and forth across the vessel in response to commands issued from the controller; and wherein a profile of a solids bed in the slurry can be determined from the results of a plurality of conductivity measurements of the solids throughout the vessel.

2. A solids measurement system as defined by claim 1 wherein said extension means includes:
   a rod having said sensor coupled at one end thereof;
   an actuator coupled to a support extending across said vessel; and
   said rod being coupled to said actuator for movement between a raised and lowered position in response to commands issued from said controller.

3. A solids measurement system as defined by claim 2 wherein said actuator is movable back and forth along said support.

4. A solids measurement system as defined by claim 2 wherein said actuator is a stepper motor.

5. A solids measurement system as defined by claim 1 wherein said extension means includes:
   a reel rotatably coupled to a mounting bracket;
   a length of flexible cable wound about said reel and having said sensor coupled to an end thereof;
   an actuator attached to said reel for rotating said wheel, thereby causing said flexible cable and said sensor to move in said first or second direction;
   a sheeve coupled for rotation to said mounting bracket and over which said flexible cable is positioned such that said sensor can be raised or lowered into the slurry; and
   a rotary encoder attached to said mounting bracket proximate said flexible cable for generating signals receivable by said controller indicative of the number of rotations of said sheeve and thereby the amount by which said cable has been moved relative to the vessel.

6. A solids measurement system as defined by claim 5 wherein said actuator is a manual handle.

7. A solids measurement system as defined by claim 5 wherein said actuator is a stepper motor.

8. A solids measurement system as defined by claim 1 wherein:
   said extension means includes a pantograph mechanism having said sensor coupled at one end thereto;
   drive means in communication with said pantograph mechanism for causing said pantograph mechanism to move said sensor in said first or second directions in response to commands issued from said controller.

9. A solids measurement system as defined by claim 8 wherein said drive means includes a cylinder having a rod slidably mounted therein and attached at an end thereof to said pantograph mechanism, said rod being moveable between an extended and retracted position, causing said pantograph mechanism to move in said first and second directions.

10. A solids measurement system as defined by claim 9 wherein said cylinder is pneumatic.

11. A solids measurement system as defined by claim 9 wherein said cylinder is hydraulic.

12. A solids measurement system as defined by claim 9 wherein said rod moves a first distance in response to commands issued from said controller, and said pantograph mechanism causes said sensor to move a second distance, said second distance being greater than said first distance.

13. A solids measurement system as defined by claim 7 wherein said second distance is approximately six times larger than said first distance.

14. A solids profile measurement system for determining the quality of a solids bed formed from a liquid-solid slurry along a lower surface of a vessel containing the slurry, the vessel forming part of a piece of processing equipment, said measurement system comprising:
   a sensor adapted to generate signals indicative of a profile as measured by progressively immersing said sensor deeper into the slurry, said profile being formed by solids settling out of the slurry towards the lower surface of the vessel;
   extension means, at least a portion of which is coupled to the processing equipment and to said sensor, for effecting retrograde movement in a first direction, thereby immersing said sensor in the slurry, and for affecting movement in a second direction opposite said first direction;
   a controller in communication with said extension means and said sensor for issuing commands thereto and receiving said signals generated by said sensor;
   said extension means is movable back and forth across the vessel in response to commands issued from the controller;
   said extension means including a pantograph mechanism having said sensor coupled at one end thereto;
   drive means in communication with said pantograph mechanism for causing said pantograph mechanism to move said sensor in said first or second directions in response to commands issued from said controller; and
   wherein said drive means includes a cylinder having a rod slidably mounted therein and attached at an end thereof to said pantograph mechanism, said rod being moveable between an extended and retracted position, causing said pantograph mechanism to move in said first and second directions.

15. A solids measurement system as defined by claim 14 wherein said cylinder is pneumatic.

16. A solids measurement system as defined by claim 14 wherein said cylinder is hydraulic.

17. A solids measurement system as defined by claim 14 wherein said rod moves a first distance in response to commands issued from said controller, and said pantograph mechanism causes said sensor to move a second distance, said second distance being greater than said first distance.

18. A solids measurement system as defined by claim 17 wherein said second distance is approximately six times larger than said first distance.

19. A solids measurement system as defined by claim 14 wherein said extension means includes:
   a reel rotatably coupled to a mounting bracket;
   a length of flexible cable wound about said reel and having said sensor coupled to an end thereof;
   an actuator attached to said reel for rotating said wheel, thereby causing said flexible cable and said sensor to move in said first or second direction;
   a sheeve coupled for rotation to said mounting bracket and over which said flexible cable is positioned such that said sensor can be raised or lowered into the slurry; and
   a rotary encoder attached to said mounting bracket proximate said flexible cable for generating signals receivable by said controller indicative of the number of rotations of said sheeve and thereby the amount by which said cable has been moved relative to the vessel.

20. A solids measurement system as defined by claim 19 wherein said actuator is a manual handle.

21. A solids measurement system as defined by claim 19 wherein said actuator is a stepper motor.

* * * * *

UNITED STATES PATENT AND TRADEMARK OFFICE
CERTIFICATE OF CORRECTION

PATENT NO.    : 6,480,009 B1
DATED         : November 12, 2002
INVENTOR(S)   : Gelfand et al.

It is certified that error appears in the above-identified patent and that said Letters Patent is hereby corrected as shown below:

<u>Title page,</u>
Item [*] Notice:, "Subject to any disclaimer, the term of this patent is extended or adjusted under 35 USC 154(b) by (3) days", delete the phrase "by 3 days" and insert -- by 0 days --

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,480,009 B1
DATED : November 12, 2002
INVENTOR(S) : Gelfand et al.

It is certified that error appears in the above-identified patent and that said Letters Patent is hereby corrected as shown below:

Column 5,
Line 60, please delete "claim 7" and insert -- claim 12 --.

Signed and Sealed this

Fourth Day of November, 2003

JAMES E. ROGAN
*Director of the United States Patent and Trademark Office*